United States Patent
Yoo et al.

(10) Patent No.: US 11,638,553 B1
(45) Date of Patent: May 2, 2023

(54) SKIN CONDITION ANALYZING AND SKIN DISEASE DIAGNOSIS DEVICE

(71) Applicant: LULULAB INC., Seoul (KR)

(72) Inventors: Sangwook Yoo, Seoul (KR); Yongjoon Choe, Seoul (KR); Seong Taek Kim, Gyeonggi-do (KR); Sijun Roh, Gyeonggi-do (KR); Pil Soo Kim, Seoul (KR)

(73) Assignee: LULULAB INC., Seoul (KR)

( * ) Notice: Subject to any disclaimer, the term of this patent is extended or adjusted under 35 U.S.C. 154(b) by 0 days.

(21) Appl. No.: 17/732,615

(22) Filed: Apr. 29, 2022

(51) Int. Cl.
| | |
|---|---|
| G06K 9/00 | (2022.01) |
| A61K 35/12 | (2015.01) |
| A61B 5/00 | (2006.01) |
| A61B 5/107 | (2006.01) |
| G06V 10/44 | (2022.01) |
| G16H 50/20 | (2018.01) |
| G06F 3/0488 | (2022.01) |
| G06T 7/00 | (2017.01) |
| G16H 50/50 | (2018.01) |
| A61B 90/30 | (2016.01) |

(52) U.S. Cl.
CPC .......... *A61B 5/441* (2013.01); *A61B 5/0075* (2013.01); *A61B 5/0079* (2013.01); *A61B 5/1079* (2013.01); *A61B 5/7275* (2013.01); *A61B 5/743* (2013.01); *A61B 5/7435* (2013.01); *G06F 3/0488* (2013.01); *G06T 7/0012* (2013.01); *G06V 10/446* (2022.01); *G16H 50/20* (2018.01); *G16H 50/50* (2018.01); *A61B 2090/309* (2016.02); *G06T 2207/30088* (2013.01)

(58) Field of Classification Search
CPC .................................. G06K 9/00; A61K 35/12
USPC ........ 382/100, 103, 106–108, 118, 128, 154, 382/162, 172–173, 181, 189–191, 203, 382/209, 219, 224, 254, 276, 285–291, 382/295, 312, 321, 274, 305, 155; 600/556, 557
See application file for complete search history.

(56) References Cited

U.S. PATENT DOCUMENTS

| | | | |
|---|---|---|---|
| 9,058,765 B1 * | 6/2015 | Mallick | G06Q 30/0256 |
| 11,232,290 B2 * | 1/2022 | McDuff | A61B 5/165 |
| 2019/0125249 A1 * | 5/2019 | Rattner | A61B 5/0077 |
| 2020/0037882 A1 * | 2/2020 | Westerhof | A61B 5/0077 |
| 2020/0383629 A1 * | 12/2020 | Yoo | A61B 5/742 |
| 2022/0254189 A1 * | 8/2022 | Dissanayake | A61B 5/445 |

FOREIGN PATENT DOCUMENTS

KR    10 2052722 B1    12/2019

* cited by examiner

*Primary Examiner* — Seyed H Azarian
(74) *Attorney, Agent, or Firm* — Sughrue Mion, PLLC

(57) ABSTRACT

The present invention relates to a device for skin condition analysis and skin disease diagnosis.
The skin condition analysis and skin disease diagnosis device according to the present invention is an all-in-one type device that can perform not only cosmetic skin condition analysis but also diagnosis of medical skin disease items.

9 Claims, 8 Drawing Sheets

[FIG. 1]
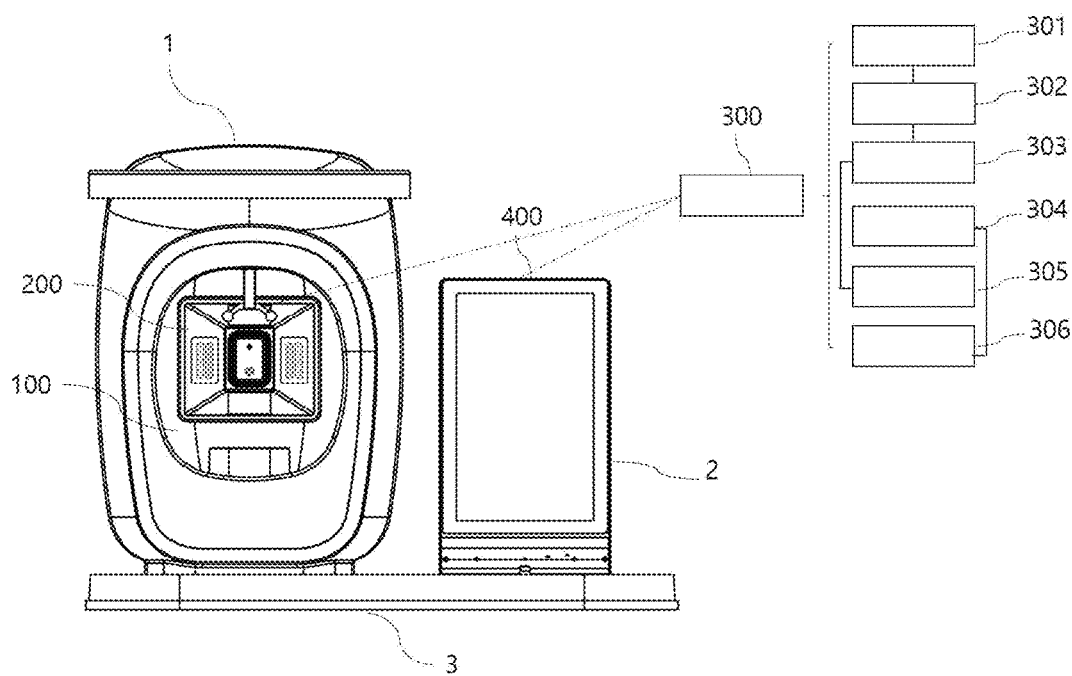

[FIG. 2]
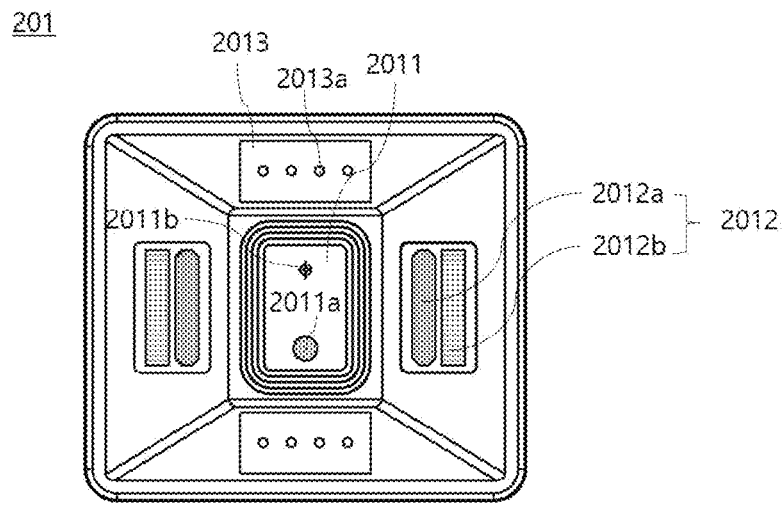
[FIG. 3]
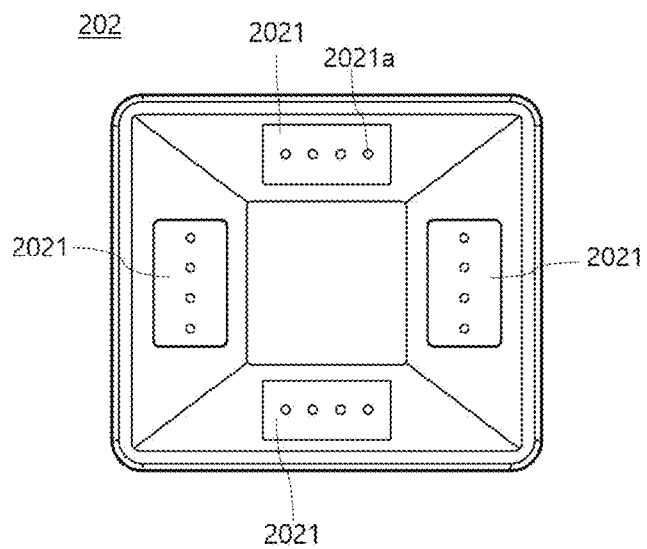

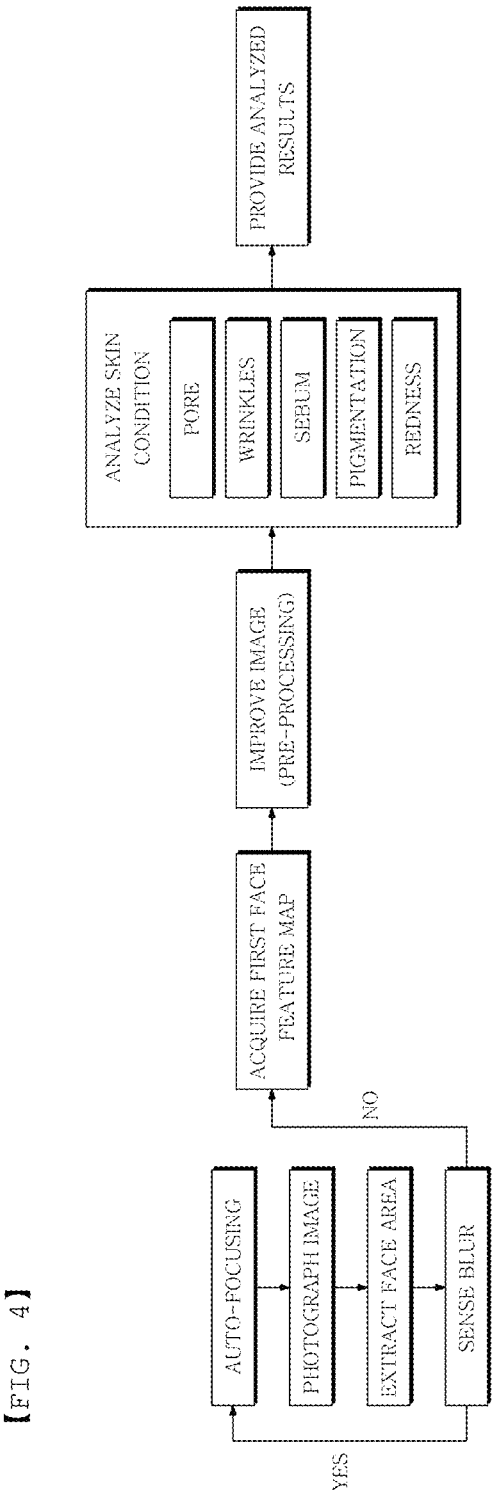

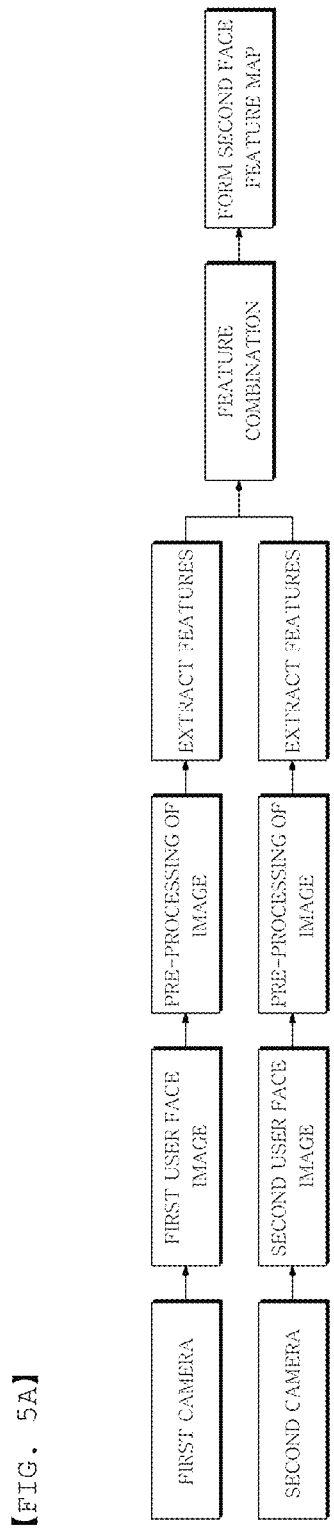
[FIG. 5A]

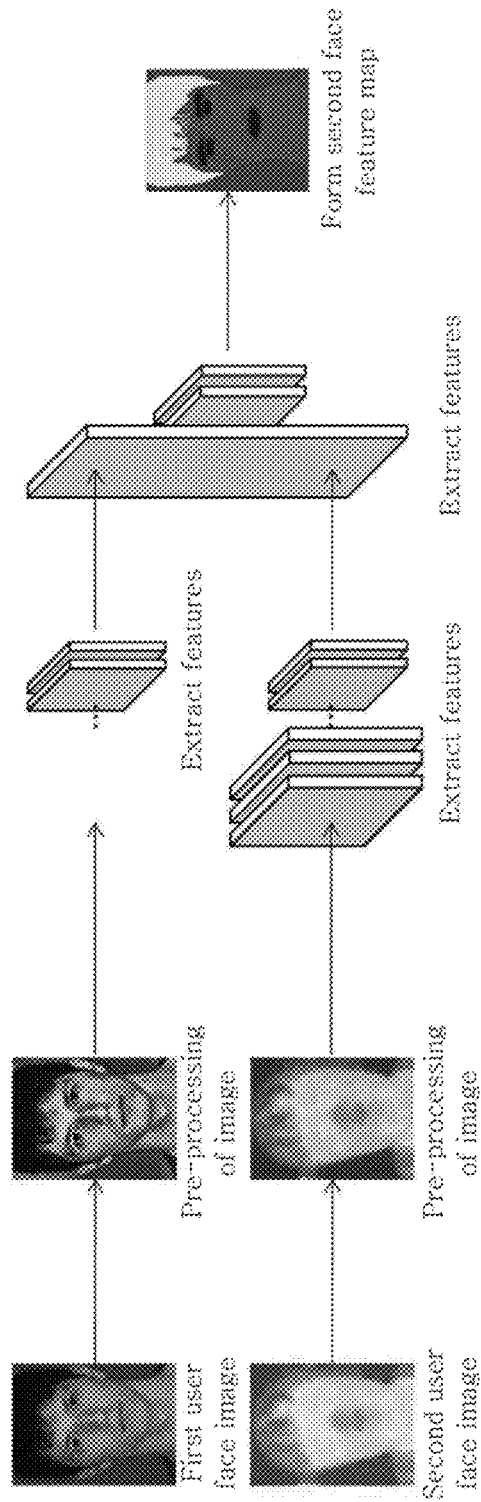

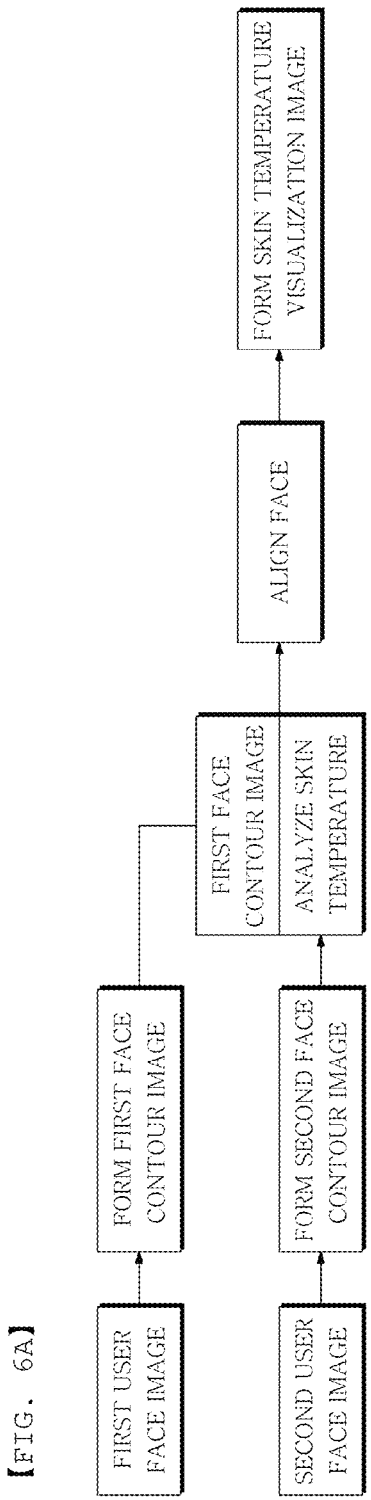
[FIG. 6A]

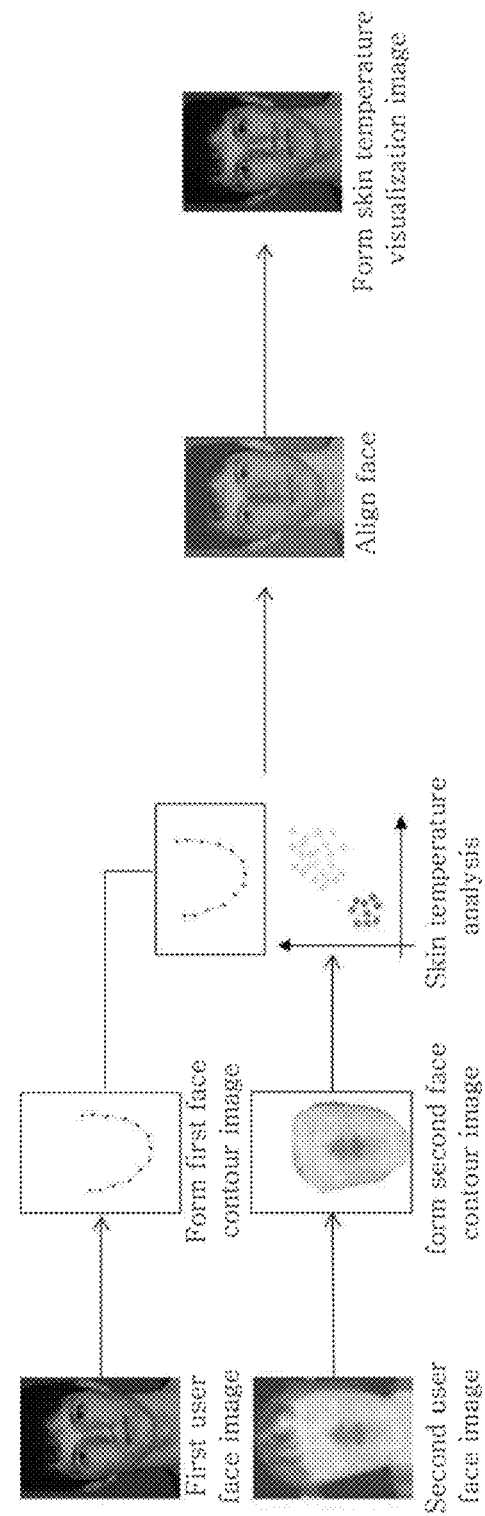
[FIG. 6B]

[FIG. 7]
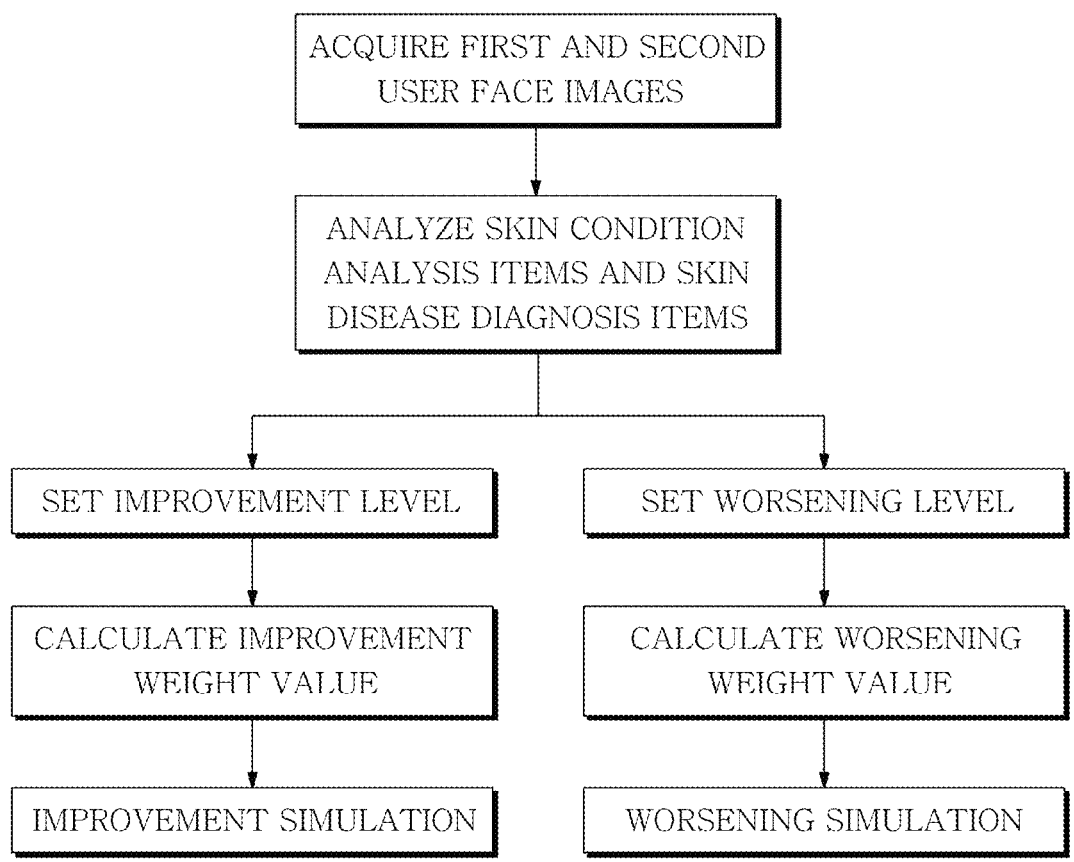

SKIN CONDITION ANALYZING AND SKIN DISEASE DIAGNOSIS DEVICE

TECHNICAL FIELD

The present invention relates to a device for skin condition analysis and skin disease diagnosis.

Specifically, the present invention relates to an all-in-one type device for skin condition analysis and skin disease diagnosis that can perform not only cosmetic skin condition analysis but also diagnosis of medical skin disease items in a single device.

BACKGROUND ART

Recently, with increased interest in beauty, interest in skin beauty of a user's face is also increasing. In particular, a skin condition measurement apparatus for photographing the skin of the user's face and analyzing a variety of skin items (e.g., wrinkles, pores, acne, etc.) on the face has been developed.

The conventional skin condition analysis apparatus and system is mainly a cloud-based two (2)-layer system that transmits the user's face image measured through a portable or non-portable device to a cloud server then provides a result analyzed through an analysis model in the cloud system to the user. In this regard, the cloud-based skin condition analysis apparatus and system involve a variety of problems including a security problem such as exposure of personal information or a problem of decrease in data processing speed.

On the other hand, the conventional skin condition measurement apparatus and system may only measure some items for analysis of cosmetic skin conditions such as pores, sebum, wrinkles, pigmentation or redness, however, entails technical limitations in regard to analysis of major skin disease items such as atopy, psoriasis, acne or leukoplakia (vitiligo), etc.

Further, apparatuses for measurement or analysis of skin conditions with application of artificial intelligence (AI) models, for example, deep learning or machine learning, have recently been developed. However, there is still a technical problem in development of a skin disease analysis device that performs highly reliable diagnosis of skin diseases, and recommends customized products based on the diagnosis or provides comprehensive prescription and skin care guides, therefore, is useful in desired places such as specialized dermatology clinics.

PRIOR ART DISCLOSURE

Patent Document (Patent Document 1.) Korean Patent Publication 10-2052722

DISCLOSURE

Technical Problem

The present invention provides a device for skin condition analysis and skin disease diagnosis that performs not only cosmetic skin condition analysis but also diagnosis of medical skin disease items, and then can provide a user with the result of the above analysis and diagnosis.

Further, the present invention provides a device for skin condition analysis and skin disease diagnosis that visualizes a temperature for each region of the user's face by mapping a skin temperature and provides the visualized temperature.

Moreover, the present invention provides a device for skin condition analysis and skin disease diagnosis that visually provide improvement and worsening simulation of each item based on a result of the skin condition analysis and a result of the skin disease diagnosis to the user.

Technical Solution

The present invention has been devised to solve the above problems, and relates to a device for skin condition analysis and skin disease diagnosis.

The device for skin condition analysis and skin disease diagnosis may include: a face interpolation region having a space in which the face of a user ("user face") is inserted and secured; a photographing module that is designed to be placed in the face interpolation region and to acquire first to third user face images for analyzing skin condition analysis items and skin disease diagnosis items; a processor that is designed to execute analysis of the skin condition analysis items including wrinkles, pigmentation, redness, sebum and pores using the above first user face image, and also execute diagnosis of the skin disease diagnosis items including acne, atopy, psoriasis, rash and leukoplakia (vitiligo) using the first and second user face images; and a rotational touch display that provides the user with the analysis results of the skin condition analysis items and the diagnosis results of the skin disease diagnosis items executed in the above processor. Further, the photographing module may include: a module front region in which: a photographing unit including a first camera designed to acquire the first user face image while having a first polar film disposed on front of the first camera, and a second camera designed to acquire the second user face image; a first white light emitting light source unit including a white light emitting light source (1a) ("first white light source (1a)") that has a second polar film disposed on front of the first white light source (1a) with the same polar axis as that of the first polar film, as well as another white light emitting light source (1b) ("first white light source (1b)") that has a third polar film disposed on front of the first white light source (1b) with a polar axis different from that of the first polar film; and a UV light emitting light source unit including a UV light emitting light source ("UV light source") that has a visible light shielding filter disposed on front of the UV light source, are provided; and a module rear region as a rear area of the module front region, in which a second white light emitting light source unit including a second white light emitting light source ("second white light source") disposed on a site corresponding to the first white light source and the UV light source is provided. Further, the processor may include: an autofocusing unit that controls the first camera to form autofocusing on the user face and photograph the same; a blur sensor unit to determine whether the first user face image exceeds a preset blur value; a first deep learning unit that executes encoding to extract features of a face area after extracting the face area from the first user face image acquired by the first camera and having passed through the blur sensor unit and then executes decoding to acquire a first face feature map provided with a class value set for each pixel; a second deep learning unit that forms a second face feature map through feature combination of an encoding result for extracting features in regard to an extracted face area after extracting the face area from the first user face image acquired by the first camera and another encoding result in regard to an extracted face area after extracting the face area from the second user face image acquired by the second camera; a skin condition analysis unit that executes analysis of skin condition analysis items including wrinkles, pigmentation, redness, sebum and pores using the first face feature map; and a skin disease diagnosis unit that executes diagnosis of skin disease diagnosis items including acne, atopy, psoriasis, rash and leukoplakia (vitiligo) using the second face feature map.

In one embodiment, the face interpolation region may further include a reflection mirror existing on the module rear region side. In this case, the second white light source may be reflected by the reflection mirror to thus indirectly irradiate the user.

In one embodiment, the photographing unit of the photographing module may include: a first camera that is designed to acquire a two-dimensional user face image having the number of pixels of 2 millions or more as the first user face image; and a second camera that is designed to acquire an IR temperature map image as the second user face image.

In one embodiment, the module front region may include: the photographing unit positioned in the center thereof; a pair of the first white light sources (1a) and (1b) positioned on both of left and right sides of the photographing unit; and the UV light source positioned on top and bottom sides of the photographing unit. Further, the module rear region may include the second white light source in a site corresponding to the first white light source (1a), the first white light source (1b) and the UV light source.

In one embodiment, the second deep learning unit may perform pre-processing of the first user face image and the second user face image, respectively, by conducting any one or more among point processing (pixel value transform), spatial domain transform, frequency domain transform and morphological operation, followed by executing encoding and decoding the pre-processed product.

In one embodiment, the processor may further include a skin temperature mapping unit that extracts a face contour from the first user face image to form a first face contour image, extracts a face contour from the second user face image to form a second face contour image, and then, forms a skin temperature visualization image by aligning a result of skin temperature analysis according to the second face contour image on the first face contour image.

In one embodiment, the skin temperature mapping unit may extract the face contour from the first user face image through landmark detection to form the first face contour image, and extract the face contour from the second user face image through Haar-like feature to form the second face contour image.

In one embodiment, the processor may further include a simulation unit that creates simulation images for improvement and worsening of skin conditions along with solutions for improvement and prescription of the skin conditions based on the results of the skin condition analysis and the skin disease diagnosis in the skin condition analysis unit and the skin disease diagnosis unit.

In one embodiment, the simulation unit may process individual pixel values in the first user face image according to weight values in stages of the improvement and worsening relative to the results of the skin condition analysis and skin disease diagnosis, so as to create the simulation images for the skin improvement and worsening.

In one embodiment, the rotational touch display may be provided with a rotary means at the bottom end thereof and be designed to be rotatable by 360 degrees.

Advantageous Effects

The skin condition analysis and skin disease diagnosis device of the present invention may more accurately execute analysis of cosmetic skin condition analysis items and diagnosis of medical skin disease diagnosis items of a user than ocular inspection and palpation of a specialist, and may instantly visualize and provide the executed results to the user.

The skin condition analysis and skin disease diagnosis device of the present invention may visually provide a temperature distribution or condition for each face area to the user.

The skin condition analysis and skin disease diagnosis device of the present invention may visually provide improvement and worsening simulation for each item according to a result of the skin condition analysis and a result of the skin disease diagnosis to the user.

Of course, the scope of the present invention is not limited by the above effects.

DESCRIPTION OF DRAWINGS

FIG. 1 is a structural-block combined diagram showing the skin condition analysis and skin disease diagnosis device of the present invention.

FIGS. 2 and 3 are diagrams more specifically illustrating structures of the front region (FIG. 2) and the rear region (FIG. 3), respectively, of the photographing module according to the present invention.

FIG. 4 is a block diagram specifically illustrating a process of executing analysis for skin condition analysis items by the skin condition analysis and skin disease diagnosis device of the present invention.

FIGS. 5a and 5b are a flow block diagram (a) and a flow illustration diagram (b) specifically illustrating a process of executing analysis for skin disease diagnosis items, respectively, by the skin condition analysis and skin disease diagnosis device of the present invention.

FIGS. 6a and 6b are a flow block diagram (a) and a flow illustration diagram (b) specifically illustrating a process of forming skin temperature visualization images, respectively, by the skin temperature mapping unit in the processor according to the present invention.

FIG. 7 is a block diagram specifically illustrating a process of creating simulation images for skin improvement and worsening by the simulation unit in the process according to the present invention.

DETAILED DESCRIPTION OF PREFERRED EMBODIMENTS OF INVENTION

Hereinafter, the present invention will be described in more detail with reference to the drawings and examples.

In the present specification, singular expressions include plural expressions unless otherwise specified.

The terms used in the present specification have been selected from general terms currently and widely used as possible while considering functions in the present invention, but this may vary according to the intention or precedent of a technician working in the field, the emergence of new technologies, and the like. Further, in specific cases, there are terms arbitrarily selected by the applicant and, at this time, the meanings of the terms will be described in detail in the corresponding description of the invention. Therefore, the terms used in the present invention should be defined based on the meanings of the terms and the contents throughout the present invention, instead of simple names of the terms.

Since the embodiments of the present invention can apply various transformations and have different examples, specific embodiments are illustrated in the drawings and will be concretely stipulated in the detailed description. However, this is not intended to limit the scope of the invention to the specific embodiments but should be understood to include all the transformations, equivalents and substitutes included in the spirit and technical scope of the invention. In the description of the embodiments, if it is determined that a concrete description of related and known art may obscure the subject matter, the detailed description thereof will be omitted.

In the present specification, terms such as "first" and "second" may be used to describe different elements, but these elements should not be limited by the terms. In fact, the terms are used only for the purpose of distinguishing one component from another component.

In the present specification, terms such as "comprise" or "consist of" are intended to designate the presence of features, numbers, steps, actions, components, parts or combinations thereof described in the specification, but do not preclude possible existence or addition of one or more other features, numbers, steps, actions, components, parts or combinations thereof.

In the present specification, the terms of "module" or "unit" has each configuration to perform at least one function or operation, and may be implemented as hardware or software or a combination of hardware and software. Further, a plurality of "modules" or a plurality of "units" may be operated and controlled by at least one processor except for a "module" or "unit" that needs to be implemented with specific hardware.

Hereinafter, the skin condition analysis and skin disease diagnosis device of the present invention will be described in more detail with reference to the accompanying drawings.

The skin condition analysis and skin disease diagnosis device of the present invention is a device that analyzes skin conditions and whether a disease occurs, based on a face image photographed by a camera after a user secures the face inside the device having a predetermined morphology.

The skin condition analysis and skin disease diagnosis device of the present invention may perform not only analysis of cosmetic skin conditions but also medical skin diagnosis based on a plurality of user face images acquired by multiple cameras and a convolutional neural network-based deep learning model to analyze the above images. Herein, the present invention is characterized in that results of the above skin condition analysis and the skin diagnosis are provided by a single device.

Further, the skin condition analysis and skin disease diagnosis device of the present invention may provide a skin temperature mapping result and a result of simulation according to improvement/worsening of the condition, and can instantly visualize and provide the above results to the user.

FIG. 1 is a structural-block combined diagram showing the skin condition analysis and skin disease diagnosis device of the present invention.

As illustrated in FIG. 1, the skin condition analysis and skin disease diagnosis device of the present invention may include: a photographing and diagnosis unit 1 that photographs a user's face ("user face") and executes skin condition analysis and skin disease diagnosis; a display unit 2 that visually provides a result acquired from the photographing and diagnosis unit 1 to the user; and a support member 3 to integrally combine the photographing and diagnosis unit 1 with the display unit 2. Although FIG. 1 shows the photographing and diagnosis unit 1 at the left side and the display unit 2 at the right side, this is only an example according to the present invention, and therefore, positions and configurations of the photographing and diagnosis unit 1 and the display unit 2 are possibly altered and should not be restrictedly interpreted as being shown in FIG. 1.

The photographing and diagnosis unit 1, the display unit 2 and the support member 3 may include each separate configuration of the skin condition analysis and skin disease diagnosis device according to the present invention.

Specifically, the photographing and diagnosis unit 1 may include a face interpolation region 100 and a photographing module 200, while the display unit 2 may include a rotational touch display 400. Further, the processor 300 may be included in the photographing and diagnosis unit 1 or the display unit 2.

The face interpolation region 100 is a region in which a face area of the user is secured and positioned, and may be provided with a space of a typical non-portable skin condition analysis device in which the user face is inserted and secured.

In one embodiment, the face interpolation region 100 may include a head fixing area and a chin fixing area, wherein the head fixing area and the chin fixing area have a role of securing a top end of the head (a forehead portion) and the chin portion of the user, respectively.

Meanwhile, a module rear region 202 of the photographing module 200 of the present invention is provided with a second white light emitting light source unit 2021. The face interpolation region 100 may further include a reflection mirror that allows a light source in the second white light emitting light source unit 2021 to act as an indirect light source so as to indirectly irradiate the user face during photographing.

In one embodiment, the face interpolation region 100 may further include a reflection mirror existing on the module rear region 202. In this case, a second white light emitting light source ("second white light source"; 2021a) may be reflected by the above reflection mirror so as to indirectly irradiate the user.

A morphology, shape and standard of the reflection mirror are not particularly limited so long as these correspond to a structure or morphology of the face interpolation region 100 and allow the second white light source (2021a) present in the module rear region 202 to indirectly irradiate the user.

Inside the face interpolation region 100, a photographing module 200 is positioned.

The photographing module 200 is a configuration to perform analysis of skin condition analysis items and diagnosis of the skin disease diagnosis items, and may be positioned in the face interpolation region 100 and designed to acquire first and second user face images for analyzing the skin condition analysis items and the skin disease diagnosis items. In this regard, the first and second user face images are photographed and acquired, respectively, by different devices (cameras), which are single images to be used for analysis of the skin condition analysis items or combined images to be used for diagnosis of the skin disease diagnosis items.

The photographing module 200 may include a module front region 201 disposed in the user face direction and a module rear region 202 disposed in the opposed direction of the user face direction.

Referring to FIG. 2, the module front region 201 will be described in more detail. Specifically, the module front region 201 may include: a photographing unit 2011 provided with a first camera 2011a that is designed to acquire the first user face image and has a first polar film disposed on front of the first camera, as well as a second camera 2011b that is designed to acquire the second user face image; a first white light emitting light source unit 2012 including a white light emitting light source ("first white light source (2012a)") that has a second polar film disposed on front of the first white light source (2012a) with the same polar axis as that of the first polar film, as well as another white light emitting light source ("first white light source (2012b)") that has a third polar film disposed on front of the first white light source (2012b) with a polar axis different from that of the first polar film; and a UV light emitting light source unit 2013 including a UV light emitting light source ("UV light source") that has a visible light shielding filter disposed on front of the UV light source.

The photographing unit 2011 may include the first camera 2011a and the second camera 2011b, which are designed to acquire the first and second user face images.

The first camera 2011a may be a camera having the number of 2 million pixels or 8 million pixels or more in order to obtain a high-definition two-dimensional user face image of FHD or UHD level or higher. The high-definition two-dimensional user face image acquired by the first camera 2011a is the first user face image and may be used for analyzing the skin condition analysis items and the skin disease diagnosis items.

The second camera 2011b may be an IR camera to acquire IR temperature map image in relation to the user face. The IR temperature map image acquired by the IR camera may be used for analyzing skin disease diagnosis items such as atopy, psoriasis, acne, rash, etc., which are be distinguishable through thermal sensation, along with the second-dimensional face image.

The photographing unit 2011 may be positioned in the center or one side of the module front region 201, preferably, as shown in FIG. 2, positioned in the center of the module front region 201.

The first white light emitting light source unit 2012 may include a first white light source 2012a which has a second polar film positioned on front of the same with the same polar axis as that of the first polar film, as well as another white light source 2012b which has a third polar film positioned on front of the same with a polar axis different from that of the first polar film.

The first white light source (1a) 2012a is a light source in which the second polar film having the same polar axis as that of the first polar film is disposed on front of the same so that it emits light when photographing in normal mode by the first camera 2011a, that is, so called "day light illuminant" which is a light source having a color temperature of 3500 to 6500 K.

The first white light source (1b) 2012b is a light source in which the third polar film having a polar axis different from that of the first polar film is disposed on front of the same so that it emits light when photographing in polar mode of light reflection removal mode by the first camera 2011a, that is, may be a light source having the same color temperature as of the first white light source (1a) 2012a. The polar axis of the third polar film may be perpendicular to that of the first polar film at a right angle.

The number or position of the first white light source (1a) 2012a and the first white light source (1b) 2012b, respectively, is not particularly limited. For example, as shown in FIG. 2b, a pair of the first white light source (1a) 2012a and the first white light source (1b) 2012b may be aligned on the left and right sides of the photographing unit 2011 positioned in the center of the module front region 201, respectively.

The UV light emitting light source unit 2013 may include a UV light source 2013a in which a visible light shielding filter is disposed on front of the same.

The UV light source 2013a is a light source emitting light when photographing in UV pass mode by the first camera 2011a, for example, may be a light source to emit UVA light or UVB light.

The number or position of the UV light source 2013a is not particularly limited, for example, as shown in FIG. 2, the UV light sources may be each provided as a group on the top and bottom sides of the photographing unit 2011 disposed in the center of the module front region 201, respectively.

On the opposed side of the module front region 201 in the opposed direction of the user face direction, a module rear region 202 is positioned.

Referring to FIG. 3, the module rear region 202 will be described in more detail. The module rear region 202 may include a second white light emitting light source unit 2021 including a second white light emitting light source ("second white light source"; 2021a) which is positioned to correspond to the UV light source 2013 and the first white light source 2012. That is, the module rear region 202 may be provided with each group of second white light sources 2021a, respectively, on top and bottom and left and right sides of an area corresponding to the photographing unit 2011 disposed in the center of the module front region 201.

Meanwhile, the second white light source 20221a included in the module rear region 202 has indirect light reflected by the reflection mirror, and thus, may indirectly irradiate the user when photographing the user face.

The first and second user face images obtained by the photographing module 200 may be analyzed by the processor 300.

The processor 300 may control action of each component and execute analysis of skin condition analysis items and diagnosis of skin disease diagnosis items using the first and second user face images.

Specifically, the processor 300 may be designed to execute analysis of the skin condition analysis items including wrinkles, pigmentation, redness, sebum and pores based on the first user face image, and further execute diagnosis of the skin disease diagnosis items including acne, atopy, psoriasis, rash, dermatitis and leukoplakia (vitiligo).

More specifically, the processor 300 may include: an auto-focusing unit 301 that controls the first camera 2011a to form auto-focusing on the user face and photograph the same; a blur sensor unit 302 to determine whether the first user face image exceeds a preset blur value; a first deep learning unit 303 that executes encoding to extract features of a face area after extracting the face area from the first user face image acquired by the first camera 2011a and having passed through the blur sensor unit 302 and then executes decoding to acquire a first face feature map provided with a class value set for each pixel; a second deep learning unit 304 that forms a second face feature map through feature combination of an encoding result for extracting features in regard to an extracted face area after extracting the face area from the first user face image acquired by the first camera 2011a and another encoding result in regard to an extracted face area after extracting the face area from the second user face image acquired by the second camera 2011b; a skin condition analysis unit 305 that executes analysis of skin condition analysis items including wrinkles, pigmentation, redness, sebum and pores using the first face feature map; and a skin disease diagnosis unit 306 that executes diagnosis of skin disease diagnosis items including acne, atopy, psoriasis, rash and leukoplakia (vitiligo) using the second face feature map.

The auto-focusing unit 301 has a role of controlling the first camera 2011*a* of the user to form auto-focusing on the user face when photographing the user face for skin condition analysis. Through the auto-focusing unit 301, only the face area of the user may be effectively extracted and analyzed by the processor 300.

The blur sensor unit 302 is a configuration to determine whether the image obtained by the first camera 2011*a* when photographing the user face exceeds a preset blue value, and thus may have a role of filtering unstably or unclearly photographed images of the user face and then leading to re-photographing. Accordingly, when the photographed user face image exceeds the preset blur value of the blur sensor unit 302, this image could not be used to analyze skin conditions, instead, the processor 300 controls the first camera 2011*a* through the auto-focusing unit 301 and may induce re-photographing while auto-focusing.

The first deep learning unit 303 has a configuration of implementing a convolutional neural network-based deep learning model that acquires the first face feature map based on the first user face image that is used for skin condition analysis through the blur sensor unit 302.

Specifically, the deep learning unit 303 may involve application of a modified Xception encoding module as the encoding module and a DeepLabv3+ decoding module as the decoding module.

More specifically, the deep learning unit 303 may: extract a face area from the first user face image; execute encoding that performs regular convolution operation, Xception operation and Rethinker operation of user face image data in order to extract features of the extracted face area, thereby creating a feature map; and form a first user face feature map through a convolutional neural network-based deep learning algorithm to execute decoding that concatenates a feature map having the corresponding dimension after ASPP (Atrous Spatial Pyramid Pooling) operation and up-sampling of the above created feature map. Further, the Rethinker operation described above may include a SE block provided with a squeeze operation part and an excitation operation part, as well as a locally constructed convLSTM layer or a three-dimensional Conv3D layer, thereby enabling extraction of a correlation to skin condition analysis item objects within a local space as well as collection of wide spatial information. On the other hand, terms such as the regular convolution operation, Xception operation, Rethinker operation, locally constructed convLSTM layer, three-dimensional convolution layer (Conv3D layer), etc. stated in the present specification are technical terms substantially widely used by those skilled in the convolutional neural network field, and therefore, it would be construed that these terms have the definition and meanings generally understood by those skilled in CNN technical fields unless otherwise stated in the present specification.

According to the configurations of the first deep learning unit 303 as described above, it is possible to accurately analyze the skin condition and, in particular, to form an image for skin condition analysis, by which results close to the ocular inspection and palpation by specialists can be deduced through application of a deep learning algorithm that considers a correlation between detection objects.

The first face feature map image acquired by the first deep learning unit 303 is transmitted to the skin condition analysis unit 305 and used to analyze skin condition analysis items including wrinkles, pigmentation, redness, sebum and pores. At this time, in order to improve or enhance the image, the first deep learning unit 303 may further execute a predetermined pre-processing.

In one embodiment, the first deep learning unit 303 may perform pre-processing of the first user face image by executing any one or more among point processing (pixel value transform), spatial domain transform, frequency domain transform and morphological operation, followed by executing encoding and decoding the pre-processed product.

Referring to FIG. 4, a processor for executing analysis of skin condition analysis items by the skin condition analysis and skin disease diagnosis device according to the present invention will be described in more detail. Specifically, the process may include: acquiring the first user face image by the first camera 2011*a* that is auto-focused by the control of the auto-focusing unit 301; extracting a face area from the acquired first user face image; and, after determining whether the acquired first user face image exceeds a preset blur value through the blur sensor unit 302, executing the encoding, decoding and pre-processing in order to obtain a first face feature map by the first deep learning unit 303 if the first user face image does not exceed the preset blur value. Following this, the skin condition analysis items including pores, wrinkles, sebum, pigmentation and redness are analyzed by the skin condition analysis unit 305, and the analyzed results may be provided to the user through the rotational touch display 400. On the other hand, when the blur sensor unit 302 determines that the first user face image exceeds the preset blur value, the first camera 2011*a* may be controlled by the auto-focusing unit 301, which in turn induces automatic focusing and re-photographing.

The second deep learning unit 304 has a configuration of implementing a convolutional neural network-based deep learning model that acquires a second face feature map based on the first and second user face images used for skin disease diagnosis.

Similar to the first deep learning unit 303, the second deep learning unit 304 may also involve application of a deep learning algorithm that considers a correlation between detection objects.

Specifically, the second deep learning unit 304 may conduct the convolution operation, Xception operation and Rethinker operation in regard to each of the first user face image and the second user face image to thus execute separate encoding of each image, followed by executing decoding to concatenate after ASPP (Atrous Spatial Pyramid Pooling) operation and up-sampling for combination of features of the encoding results so that an algorithm to acquire the second face feature map can be applied. At this time, detailed processes of each operation module may be identical to or different from those performed in the first deep learning unit 303.

Further, the second deep learning unit 304 may further perform a predetermined pre-processing before encoding to extract features.

In one embodiment, the second deep learning unit 304 may perform pre-processing of the first user face image and the second user face image, respectively, by conducting any one or more among point processing (pixel value transform), spatial domain transform, frequency domain transform and morphological operation, followed by executing encoding and decoding the pre-processed product.

The second face feature map acquired by the second deep learning unit 304 is transmitted to the skin disease diagnosis unit 306 and used for diagnosis of the skin disease diagnosis items including atopy, psoriasis, rash, dermatitis and leukoplakia (vitiligo).

Referring to FIGS. 5*a* and 5*b*, the diagnosis executing process for the skin disease diagnosis items will be described in more detail. Specifically, the first and second user face images obtained by the first camera 2011*a* and the second camera 2011*b*, respectively, are subjected to separate encoding processes for feature extraction after conducting a predetermined pre-processing. Following this, the encoded separate results are decoded for feature combination, and then transformed into a single second face feature map, wherein the second face feature map is transmitted to the skin disease diagnosis unit 306 and used for diagnosis of the skin disease diagnosis items.

The skin condition analysis and skin disease diagnosis device of the present invention enables skin condition analysis and skin disease diagnosis in specialist level according to the above-mentioned configurations, and can directly visualize and provide a result of the above performance to a user.

The skin condition analysis and skin disease diagnosis device of the present invention may provide the user with a degree of thermal sensation of the skin as additional information, and such provision may be implemented by the skin temperature mapping unit in the processor 300.

Specifically, the processor 300 may further include a skin temperature mapping unit that extracts a face contour from the first user face image to form a first face contour image, extracts another face contour from the second user face image to form a second face contour image, and aligns a result of skin temperature analysis based on the second face contour image on the first face contour image, so as to form a skin temperature visualization image.

More specifically, the skin temperature mapping unit may extract a face contour from the first user face image through landmark detection to form a first face contour image, and extract another face contour from the second user face image through Haar-like feature to form a second face contour image. Meanwhile, the Haar-like feature refers to a technique that filters input image through a square filter mask consisting of black and white colors, followed by analyzing the same through a cascade classifier to thus extract the face contour.

Referring to FIGS. 6*a* and 6*b*, a process of forming a skin temperature visualization image by the skin temperature mapping unit will be described in more detail. Specifically, the skin temperature mapping unit may: apply landmark detection and Haar-like feature to the first and second user face images acquired by the first and second cameras 2011*a* and 2011*b*, respectively, to form first and second face contour images; align the skin temperature analysis data, which were analyzed on the basis of the second face contour image, on the first face contour image so as to form a skin temperature visualization image, which in turn provides the formed image to the user through the rotational touch display 400.

Further, the skin condition analysis and skin disease diagnosis device of the present invention may provide the result of the skin condition analysis and the skin disease diagnosis to the user and, at the same time, further provide a solution to skin condition improvement and prescription, as well as simulation images according to the solution. Such performance may be implemented in a simulation unit of the processor.

Specifically, the processor 300 may further include the simulation unit that generates not only a solution to skin condition improvement and prescription but also simulation images in regard to skin improvement and worsening, based on the results of the skin condition analysis and skin disease diagnosis in the skin condition analysis unit 305 and the skin disease diagnosis unit 306, respectively.

More specifically, the simulation unit may process separate pixel values in the first user face image according to weight values in stages of improvement and worsening for each item with respect to the results of the skin condition analysis and skin disease diagnosis, thereby creating simulation images for skin improvement and worsening.

Referring to FIG. 7, a process of creating simulation images for skin improvement and worsening by the simulation unit will be described in more detail. Specifically, the simulation unit may: set improvement or worsening levels for simulation according to the results of the skin condition analysis and skin disease diagnosis, which were performed by the skin condition analysis unit 305 and the skin disease diagnosis unit 306, respectively, based on the first and second user face images acquired by the first and second cameras 2011*a* and 2011*b*; and, after operation of the improvement or worsening weight values according to the set levels, reflect the operated result on images resulting from the skin condition analysis and the skin disease diagnosis, and then, visualize and provide the images to the user through the rotational touch display 400.

The above-described results of the skin condition analysis and the skin disease diagnosis, the skin temperature mapping result, and the simulation result for skin condition improvement/worsening may be visualized and visibly provided to the user through the rotational touch display 400.

On the other hand, the rotational touch display 400 may be designed to be rotatable in the front/rear direction, and may be provided with a rotary means at the bottom end thereof.

Specifically, the rotational touch display 400 may be designed to be rotatable by 360 degrees while having a rotary means at the bottom end thereof. At this time, the rotary means may be, for example, fixed on the support member 3 to integrally combine the photographing and diagnosis unit 1 and the display unit 2.

Since the above-described configurations are included, the skin condition analysis and skin disease diagnosis device of the present invention can perform not only analysis of cosmetic skin conditions but also diagnosis of medical skin disease items, can provide mapping information on thermal sensation of the skin and simulation images with respect to skin condition improvement/worsening, and may be advantageous as a single device capable of instantly visualizing and providing the above performance to a user.

As described above, although the present disclosure has been described by way of the specific embodiments and drawings, the present disclosure is not limited to the above embodiments, and various modifications and variations from the above description are possibly implemented by those of ordinary skill in the field to which the present disclosure pertains. Therefore, the scope of the present disclosure should not be determined by the limited embodiments, instead, should be determined by the claims to be described later as well as equivalents to the claims.

DESCRIPTION OF REFERENCE NUMERALS

1: Photographing and diagnosis unit
2: Display unit

3: Support member
100: Face interpolation region
200: Photographing module
201: Module front region
2011: Photographing unit
2011a: First camera
2011b: Second camera
2012: First white light emitting light source unit
2012a,b: First white light emitting light source ("First white light source (1a), (1b)")
2013: UV light emitting light source unit
2013a: UV light emitting light source ("UV light source")
202: Module rear region
2021: Second white light emitting light source unit
2021a: Second white light emitting light source ("Second white light source")
300: Processor
301: Auto-focusing unit
302: Blur sensor unit
303: First deep learning unit
304: Second deep learning unit
305: Skin condition analysis unit
306: Skin disease diagnosis unit
400: Rotational touch display

The invention claimed is:

1. A device for skin condition analysis and skin disease diagnosis, comprising:
a face interpolation region having a space in which the face of a user is inserted and secured;
a photographing module that is designed to be placed in the face interpolation region and to acquire first user face image and second user face image for analyzing skin condition analysis items and skin disease diagnosis items;
a processor that is designed to execute analysis of the skin condition analysis items including wrinkles, pigmentation, redness, sebum and pores using the first user face image, and also execute diagnosis of the skin disease diagnosis items including acne, atopy, psoriasis, rash and vitiligo using the first user face image and the second user face image; and
a rotational touch display that provides the user with the analysis results of the skin condition analysis items and the diagnosis results of the skin disease diagnosis items executed in the above processor,
wherein the photographing module includes:
a module front region in which: a photographing unit including a first camera designed to acquire the first user face image while having a first polar film disposed on front of the first camera, and a second camera designed to acquire the second user face image; a first white light emitting light source unit including a first white light source that has a second polar film disposed on front of the first white light source with the same polar axis as that of the first polar film, as well as a second white light source that has a third polar film disposed on front of the second white light source with a polar axis different from that of the first polar film; and an ultraviolet light emitting light source unit including an ultraviolet light source that has a visible light shielding filter disposed on front of the ultraviolet light source, are provided; and
a module rear region as a rear area of the module front region, in which a second white light emitting light source unit including a third white light source disposed on a site corresponding to the first white light source unit and the ultraviolet light source unit is provided,
wherein the processor includes:
an auto-focusing unit that controls the first camera to form auto-focusing on the face of the user and photograph the same;
a blur sensor unit to determine whether the first user face image exceeds a preset blur value;
a first deep learning unit that executes encoding to extract features of a face area after extracting the face area from the first user face image acquired by the first camera and having passed through the blur sensor unit, and then, executes decoding to acquire a first face feature map provided with a class value set for each pixel;
a second deep learning unit that forms a second face feature map through feature combination of an encoding result for extracting features in regard to an extracted face area after extracting the face area from the first user face image acquired by the first camera and another encoding result in regard to an extracted face area after extracting the face area from the second user face image acquired by the second camera;
a skin condition analysis unit that executes analysis of skin condition analysis items including wrinkles, pigmentation, redness, sebum and pores using the first face feature map;
a skin disease diagnosis unit that executes diagnosis of skin disease diagnosis items including acne, atopy, psoriasis, rash and vitiligo using the second face feature map; and
a simulation unit that creates simulation images for improvement and worsening of skin conditions along with solutions for improvement and prescription of the skin conditions based on the results of the skin condition analysis and the skin disease diagnosis in the skin condition analysis unit and the skin disease diagnosis unit, respectively.

2. The device according to claim 1, wherein the face interpolation region further includes,
a reflection mirror existing on the module rear region side, wherein the third white light source is reflected by the reflection mirror to thus indirectly irradiate the user.

3. The device according to claim 1, wherein the photographing unit of the photographing module includes,
a first camera that is designed to acquire a two-dimensional user face image having the number of pixels of 2 millions or more as the first user face image; and
a second camera that is designed to acquire an infrared temperature map image as the second user face image.

4. The device according to claim 1, wherein the module front region includes:
the photographing unit positioned in the center thereof;
a pair of the first white light source and the second white light source positioned on both of left and right sides of the photographing unit; and
the ultraviolet light source positioned on top and bottom sides of the photographing unit,
wherein the module rear region includes:
the third white light source in a site corresponding to the first white light source, the second white light source and the ultraviolet light source.

5. The device according to claim 1, wherein the second deep learning unit performs
pre-processing of the first user face image and the second user face image, respectively, by conducting any one or more among pixel value transform, spatial domain transform, frequency domain transform and morphological operation, followed by executing encoding and decoding the pre-processed product.

6. The device according to claim 1, wherein the processor further includes,
a skin temperature mapping unit that extracts a face contour from the first user face image to form a first face contour image, extracts a face contour from the second user face image to form a second face contour image, and then, forms a skin temperature visualization image by aligning a result of skin temperature analysis according to the second face contour image on the first face contour image.

7. The device according to claim 6, wherein the skin temperature mapping unit extracts the face contour from the first user face image through landmark detection to form the first face contour image, and extracts the face contour from the second user face image through Haar-like feature to form the second face contour image.

8. The device according to claim 1, wherein the simulation unit processes individual pixel values in the first user face image according to weight values in stages of the improvement and worsening relative to the results of the skin condition analysis and skin disease diagnosis, so as to create the simulation images for the skin improvement and worsening.

9. The device according to claim 1, wherein the rotational touch display is provided with a rotary means at the bottom end thereof and is designed to be rotatable by 360 degrees.

* * * * *